United States Patent [19]

Fedorov et al.

[11] Patent Number: 4,579,557
[45] Date of Patent: Apr. 1, 1986

[54] INTRAOCULAR LENS IMPLANT

[76] Inventors: Svyatoslav N. Fedorov, ulitsa Valtera Ulbrikhta, 2a, kv. 40; Valery D. Zakharov, ulitsa Dubninskaya, 6, kv. 109; Nikolai I. Oleshko, ulitsa Kibalchicha, 2/1, kv. 139, all of Moscow, U.S.S.R.

[21] Appl. No.: 605,471

[22] Filed: Apr. 30, 1984

[51] Int. Cl.[4] .............................................. A61F 2/16
[52] U.S. Cl. ...................................................... 623/6
[58] Field of Search .................................. 3/13; 623/6

[56] References Cited

U.S. PATENT DOCUMENTS 4,494,254  1/1985  Lopez ........................................ 3/13

FOREIGN PATENT DOCUMENTS 545352  5/1977  U.S.S.R. .................................... 3/13
858819  8/1981  U.S.S.R. .................................... 3/13

OTHER PUBLICATIONS

Americal IOL International Lenses (advertisement), Dec. 29, 1981, Style 115 Shepard Universal A/C IOL, Americal IOL International, 15542 Graham St., Huntington Beach, Calif.
Price List IOLAB (advertisement), Jan. 4, 1982 (2 pages) Posterior Chamber Lenses (Type 103R), IOLAB Corp., 861 South Village Oaks Drive, Covina, Calif. 91724.

*Primary Examiner*—Ronald L. Frinks
*Attorney, Agent, or Firm*—Burgess, Ryan & Wayne

[57] ABSTRACT

An intraocular lens implant comprises a lens and three support members. The support members disposed on one and the same diametrical side are made in the form of bent feet terminating in loops facing toward the periphery of the lens. The sector-shaped member is cambered toward the periphery of the lens and all support members lie in the plane of the lens.

1 Claim, 2 Drawing Figures

INTRAOCULAR LENS IMPLANT

FIELD OF THE INVENTION

The invention relates to medicine, and more particularly, to ophthalmology, and it deals specifically with an intraocular lens implant to be used to replace the natural eye lens, e.g. in treating a cataract.

BACKGROUND OF THE INVENTION

It is known that in the course of a surgical treatment of various eye diseases it is frequently necessary to remove the natural eye lens which is to be subsequently replaced by an artificial lens or intraocular lens implant. Generally the majority of such implants require an additional step of suturing support members or haptic to the iris, which is a comparatively complicated operation especially in affixing the support members to the lower part of the iris. The dislocation of the lens upon pupil dilation is not infrequent if the implant is placed into the puncture of the iris as disclosed in URSS Inventor's Certificate No. 545352, wherein an intraocular lens implant involves the provision of a lens and support feet outside the pupil area and the lens has at least one loop-shaped lug for making a suture affixing the implant to the iris.

Another intraocular lens implant disclosed in USSR Inventor's Certificate No. 858819 has been developed with the aim of facilitating the implantation of the lens and improving the reliability of its fastening. In this implant the upper loop-shaped foot is in the form of two lugs disposed opposite to each other in the horizontal plane of the lens, in the upper half thereof, and the plane of the loop-shaped foot is at an angle of 5° to 8° with respect to the lens plane for imparting a spring-like action. The implant also has a lower support foot.

The disadvantage of this implant resides in that it requires a large iridotomy (up to 4 mm long) in the upper part of the iris with subsequent application of supramide suture which substantially prolongs the operation and causes additional technical difficulties during the implantation. In addition, one cannot completely rule out the possibility of deformation of the pupil and enlargement of iridotomy in cutting the suture through thinned spherical distortions resulting from prolonged compression of the iris tissues which may cause, among other things, dislocation of the intraocular lens implant.

It is an object of the invention to provide an intraocular lens implant which ensures more reliable fastening of the implant in the patient's eye.

Another object of the invention is to simplify the technique of implantation of an intraocular lens, and the elimination of side-effects resulting from the implantation of the lens.

SUMMARY OF THE INVENTION

These and other objects are accomplished by an intraocular lens implant comprising a lens and three support members of which one is made in the form of a sector and the two, of which are disposed on one and the same side of the lens diametrically opposite to the sector. According to the invention, the members disposed on one and the same diametrical side are made in the form of feet bent in opposite directions and terminating in loops facing toward the periphery of the lens, the sector-shaped member being cambered toward the lens and all support members lying in the plane of the lens.

This design of the intraocular lens implant makes it possible to dispense with the need for making a basal iridotomy and subsequent application of a suture to the iris so that the operation time is substantially reduced, the manipulations within the anterior chamber are minimized and the injury of the endothelium of the cornea is also reduced. At the same time, the number of support points is increased thus lowering the pressure on the surrounding tissues and reducing their atrophic changes; while misalignment of the lens with respect to the optic axis of the eye and its dislocation into the vitreous body are also reduced.

BRIEF DESCRIPTION OF THE ACCOMPANYING DRAWINGS

Other objects and advantages of the invention will become apparent from the following detailed description with reference to the accompanying drawings, in which.

DESCRIPTION OF THE PREFERRED EMBODIMENT

Figure 1:
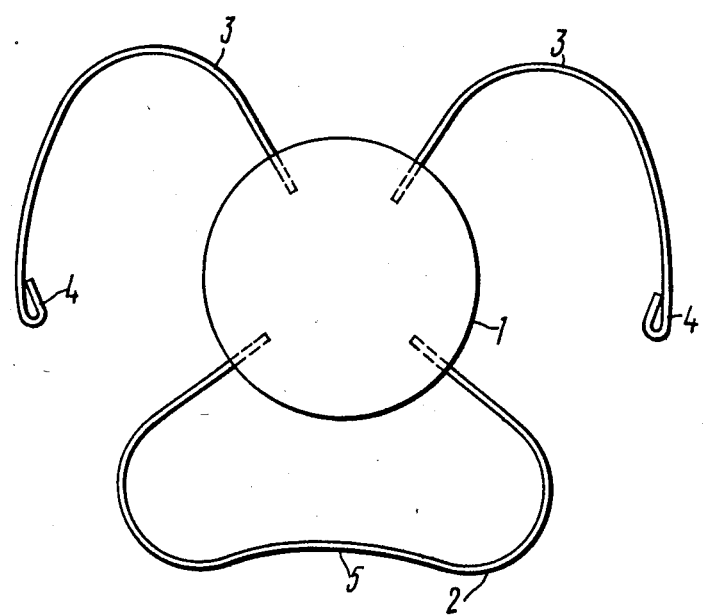
FIG. 1 is a front elevation of an intraocular lens implant according to the invention.
Figure 2:
FIG. 2 is a side elevation of the intraocular lens implant, shown in FIG. 1.

Referring now to FIGS. 1 and 2, it may be seen that an intraocular lens implant according to the invention comprises a lens 1 and three support members 2 and 3. The lens 1 may be made of a polymer such as polymethyl methacrylate and the support members may be made of a thin wire material which is inert with respect to the eye fluid. Use may be made of such materials as supramid or polypropylene.

The support member 2 is in the form of a sector having its ends secured to the lens 1 by any appropriate known means. The sector 2 extends along the periphery of the lens 1 over an arc of about 90° and is disposed in a spaced relationship with respect to its periphery. The intermediate part of the support member 2 is cambered at 5 by bending the wire to form the sector.

The support members 3 are identically shaped in the form of bent feet disposed on one and the same side diametrically opposite to said sector-shaped member 2. The two bent feet 3 are bent in opposite directions and terminate in a loop 4 defining rounded portions to avoid injury of the patient's eye during the implantation. The portions of the bent feet extending along the periphery are symmetrical with respect to the diametrical plane drawn through the center of the lens 1 and the middle of the sector 2.

The outer extremities of the bent feet 3 in the zone of the loops 4 and the extremities of the sector 2 may be on one and the same imaginary circle with the center located adjacent to the center of the lens 1.

The extension of the sector 2 is preferably greater than the distance between the points of fastening of the bent feet 3 to the lens.

The intraocular lens implant according to the invention is implanted in the following manner.

An incision is made through the cornea along the outer extremity of the limbus to form a conjunctival flap 3–4 mm wide. The pupil is caused to dilate by administering 1% phenylephrine hydrochloride into the anterior chamber. The anterior crystalline capsule is opened along the circumference with a cystotome. The nucleus of the lens is removed with a loop. The crystalline mass is washed out through a cannula with a sodium chloride solution. The insertion of the intraocular lens implant is effected by means of gripping forceps having retaining projections which urge the bent feet 3 against the lens and prevent them from unbending.

The intraocular lens implant is gripped in such a manner that the sector-shaped support member 2 should be in front.

The working part of the forceps is introduced together with the intraocular lens implant into the posterior chamber and then, using a spatula, the bent feet 3 are released one after the other from the retaining projections of the forceps so that they could unbend and take the desired position in the posterior chamber on their own. The working part of the forceps is then withdrawn. The sealing is then made by means of 6-7 interrupted sutures. For the regeneration of the anterior chamber, an isotonic solution of sodium chloride is preferebly administered into it. A continuous suture is then applied to the conjunctiva to complete the operation.

EXAMPLE 1

A female patient K aged 62 was admitted with the diagnosis OD mature cataract, age-related OS primary cataract, age-related Status on admission:

$$VOD = \frac{1}{\infty} \text{ pr.l.certa}$$

VOS=0.8 (non-correctible).

The extracapsular extraction was made with the simultaneous implantation of intraocular lens +24.0 in the right eye. The operation was conducted without complications. The post-operation inflammatory reaction was of the I degree.

Status on dismissal:

$$VOD = 0.8 \text{ c-cyl } 0.5D \text{ ax.}84° = 1.$$

Three months after VOD=1.0

EXAMPLE 2

A female patient G. aged 54 was admitted with the diagnosis OS-complicated cataract.

Status on admission:

$$VOD = 1.0.$$

$$VOS = 0.02 \text{ (non-correctible)},$$

The extracapsular extraction was made simultaneously with the implantation of the intraocular lens +22.0 OD according to the invention. The operation was conducted without complications. The postoperation inflammatory reaction was of the I degree.

Status on dismissal:

$$VOS = 0.63 \cosph + 1.0D = 0.7$$

(because of the cloudy posterior crystalline capsule).

Fundoscopy of the posterior capsule was conducted under the outpatient clinic conditions on the same day $$VOS = 0.8 \cosph + 1.0D = 1.0.$$

Implantation of the intraocular lens is recommended in case of aphakia with the intact posterior crystalline capsule and also immediately after the extracapsular extraction conducted by various techniques with cataracts of any etiology.

The contraindications to the implantation of intraocular lens are the absence of the posterior crystalline capsule of the eye or damage thereto during the surgical interference.

The use of the intraocular lens implant according to the invention makes it possible to reduce by 25% the time of the surgical interference thus enabling an increase in the number of operations during the same time. The design of the intraocular lens implant ensures high reliability of its fastening.

Although one specific embodiment only has been described, it will be apparent to those skilled in the art that various changes and modifications may be made without going beyond the spirit and scope of the invention as defined in the appended claims.

We claim:

1. In an intraocular lens implant comprising a lens and three support members of which one is made in the form of a sector and the two others are disposed on one and the same side of the lens diametrically opposite to the sector, an improvement consisting in that the support members disposed on one and the same diametrical side are made in the form of feet bent in opposite directions and terminating in loops facing toward the periphery of the lens, the sector-shaped member being cambered toward the lens and all support members lying in the plane of the lens.

* * * * *